US007414162B2

(12) United States Patent
Link et al.

(10) Patent No.: US 7,414,162 B2
(45) Date of Patent: Aug. 19, 2008

(54) WATER-SOLUBLE PHENYLENEDIAMINE COMPOSITIONS AND METHODS FOR STABILIZING ETHYLENICALLY UNSATURATED COMPOUNDS AND MONOMERS

(75) Inventors: John Link, Humble, TX (US); Sherif Eldin, Houston, TX (US)

(73) Assignee: General Electric Company, Fairfield, CT (US)

( * ) Notice: Subject to any disclaimer, the term of this patent is extended or adjusted under 35 U.S.C. 154(b) by 0 days.

(21) Appl. No.: 11/786,826

(22) Filed: Apr. 13, 2007

(65) Prior Publication Data

US 2007/0187649 A1    Aug. 16, 2007

Related U.S. Application Data

(62) Division of application No. 10/422,521, filed on Apr. 24, 2003, now abandoned.

(51) Int. Cl.
*C07C 7/20* (2006.01)
(52) U.S. Cl. .......................................................... 585/5
(58) Field of Classification Search .................. None
See application file for complete search history.

(56) References Cited

U.S. PATENT DOCUMENTS

| 3,907,745 | A | 9/1975 | Bsharah et al. |
| 4,466,905 | A | 8/1984 | Butler et al. |
| 4,774,374 | A | 9/1988 | Abruscato et al. |
| 4,929,778 | A | 5/1990 | Roling |
| 5,258,138 | A | 11/1993 | Gatechair et al. |
| 5,396,004 | A | 3/1995 | Arhancet et al. |
| 5,416,258 | A | 5/1995 | Arhancet et al. |
| 5,446,220 | A | 8/1995 | Arhancet |
| 5,489,718 | A | 2/1996 | Arhancet |
| 5,609,749 | A | 3/1997 | Yamauchi et al. |
| 6,200,461 | B1 | 3/2001 | Eldin |
| 6,337,426 | B1 | 1/2002 | Winter |
| 2001/0009968 | A1 | 7/2001 | Eldin |
| 2002/0061946 | A1 | 5/2002 | Malz, Jr. et al. |

FOREIGN PATENT DOCUMENTS

| EP | 0 594 341 A1 | 4/1994 |
| EP | 0 663 446 A2 | 7/1995 |
| EP | 1 041 062 A2 | 10/2000 |
| GB | 1113056 | 5/1968 |

*Primary Examiner*—Samuel A Barts
(74) *Attorney, Agent, or Firm*—Hoffmann & Baron, LLP

(57) ABSTRACT

Compositions and methods for inhibiting polymerization of ethylenically unsaturated monomers are provided. The compositions include a water-soluble phenylenediamine composition.

9 Claims, No Drawings

WATER-SOLUBLE PHENYLENEDIAMINE COMPOSITIONS AND METHODS FOR STABILIZING ETHYLENICALLY UNSATURATED COMPOUNDS AND MONOMERS

CROSS-REFERENCE TO RELATED APPLICATIONS

The present application is a divisional application of application Ser. No. 10/422,521, filed Apr. 24, 2003 now abandoned, the entire contents of which are incorporated herein by reference.

FIELD OF THE INVENTION

The present invention relates to water-soluble phenylenediamine compositions and methods for inhibiting polymerization of ethylenically unsaturated hydrocarbons.

BACKGROUND OF THE RELATED TECHNOLOGY

During the refining process, hydrocarbon streams are frequently exposed to elevated temperatures, which can lead to premature polymerization of the desired monomer. The premature polymerization results in reduction of the amount of the desired monomer end-products as well as a loss in efficiency caused by fouling and deposit formation within the processing equipment.

In order to reduce or prevent polymer formation, stabilizing or inhibitor compositions have been introduced into the hydrocarbon stream at or upstream of a location where polymerization is likely to occur, such as where distillation is performed.

Phenylenediamines (PDA's) are widely used as antioxidants and polymerization inhibitors. However, their use is limited to hydrocarbon streams where the PDA is soluble. A number of patents relate to the use of various PDA's, combinations of different PDA's and combinations of PDA's with other inhibitors to stabilize hydrocarbon fluids.

Among these patents is U.S. Pat. No. 6,200,461 to Eldin which describes methods and compositions for inhibiting the polymerization of ethylenically unsaturated hydrocarbons under both processing and storage conditions by the addition of combinations of aminophenol compounds and either PDA or hydroxylamine. Other combinations have also been used. These include inhibitor combinations containing a PDA with an oxime compound and a hydroxylamine as shown in U.S. Pat. No. 5,489,718 to Arhancet. Other examples include the combination of a PDA and a hydroxylamine as shown in U.S. Pat. No. 5,396,004 to Arhancet and a PDA with a hydroxytoluene compound as shown in U.S. Pat. No. 5,416,258 to Arhancet et al.

Examples of specific PDA compounds may be found in U.S. Pat. No. 4,929,778 to Roling which describes compositions including a PDA compound which has at least one N—H bond and a hindered phenol useful for inhibiting the polymerization of styrene during elevated temperature processing, storage and shipment. U.S. Pat. No. 4,774,374 to Abruscato et al. discloses an oxygenated species formed by the reaction of oxygen and an N-aryl-N'-alkyl-p-phenylenediamine.

While each of these references provides compositions and methods that reduce premature polymerization of ethylenically unsaturated monomers, they are generally limited to hydrocarbon processing and storage where they are soluble, which does not include where water is present. Therefore, the currently available PDA inhibitors do not adequately address the concerns of the prevention of premature polymerization of a monomers with water-solubility, where a water phase is present.

Therefore, it would be desirable to provide a water-soluble composition for the reducing and or preventing the polymerization of ethylenically unsaturated monomers. Desirably, the composition will include a water-soluble phenylenediamine composition which acts as an antioxidant/free-radical polymerization inhibitor.

SUMMARY OF THE INVENTION

The present invention provides a water-soluble phenylenediamine composition which also functions as an antioxidant/free-radical polymerization inhibitor. The compounds are of the following formula:

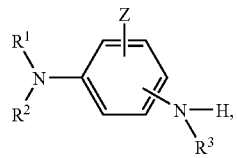

wherein at least one of $R^1$, $R^2$, and $R^3$ is

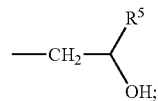

$R^1$, $R^2$ and $R^3$ are independently selected from H, alkyl, hydroxyalkyl, —O—$R^6$, —S—$R^6$, —C(O)$R^6$, —C(S)$R^6$, —N—($R^7$)($R^8$), aryl, and

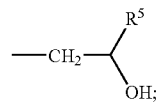

$R^5$ is selected from the group consisting of H, alkyl, hydroxyalkyl, O, S, —O—$R^6$, —S—$R^6$, —N—($R^7$)($R^8$), and aryl;

Z comprises one or more substituents selected from the group consisting of hydrogen, alkyl, alkenyl, alkynyl, cycloalkyl, cycloalkenyl, aryl, heterocyclo, —CN, —NO$_2$, —O—$R^6$, —S—$R^6$, and —N($R^7$)($R^8$); and $R^6$, $R^7$ and $R^8$ are independently selected from the group consisting of hydrogen, alkyl, alkenyl, alkynyl, cycloalkyl, cycloalkenyl, aryl and heterocyclo. Desirably, the compound corresponds the following formula:

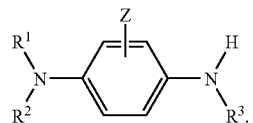

The compounds of formula (I), above, may be added to a composition including an ethylenically unsaturated monomer to produce a composition resistant to polymerization. The addition of the water-soluble phenylenediamine composition of the present invention to the monomer composition may occur during synthesis or processing or storage of the composition.

The compounds of the present invention include a reaction product of a phenylenediamine compound of the following formula:

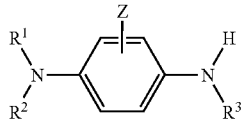

wherein at least one of $R^1$, $R^2$ and $R^3$ is H;

$R^1$, $R^2$ and $R^3$ are independently selected from the group consisting of, alkyl, hydroxyalkyl, —O—$R^6$, —S—$R^6$, —C(O)$R^6$, —C(S)$R^6$, —N—($R^7$)($R^8$), and aryl;

Z comprises one or more substituents selected from the group consisting of hydrogen, alkyl, alkenyl, alkynyl, cycloalkyl, cycloalkenyl, aryl, heterocyclo, —CN, —NO$_2$, —O—$R^6$, —S—$R^6$, and —N($R^7$)($R^8$); and $R^6$, $R^7$ and $R^8$ are independently selected from the group consisting of hydrogen, alkyl, alkenyl, alkynyl, cycloalkyl, cycloalkenyl, aryl and heterocyclo, with a heterocylic compound of the following formula:

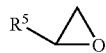

wherein $R^5$ is selected from the group consisting of H, alkyl, hydroxyalkyl, —O—$R^6$, —S—$R^6$, —N—($R^7$)($R^8$), and aryl.

Another aspect of the present invention provides a method of preparing a water-soluble phenylenediamine composition including the step of reacting a phenylenediamine compound of the following formula:

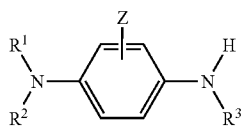

wherein at least one of $R^1$, $R^2$ and $R^3$ is H and $R^1$, $R^2$ and $R^3$ are independently selected from the group consisting of, alkyl, hydroxyalkyl, —O—$R^6$, —S—$R^6$, —C(O)$R^6$, —C(S)$R^6$, —N—($R^7$)($R^8$), and aryl;

Z comprises one or more substituents selected from the group consisting of hydrogen, alkyl, alkenyl, alkynyl, cycloalkyl, cycloalkenyl, aryl, heterocyclo, —CN, —NO$_2$, —O—$R^6$, —S—$R^6$, and —N($R^7$)($R^8$); and $R^6$, $R^7$ and $R^8$ are independently selected from the group consisting of hydrogen, alkyl, alkenyl, alkynyl, cycloalkyl, cycloalkenyl, aryl and heterocyclo, with a heterocylic compound of the following formula:

wherein $R^5$ is selected from the group consisting of H, alkyl, hydroxyalkyl, —O—$R^6$, —S—$R^6$, —N—($R^7$) ($R^8$), and aryl. Desirably, the phenylenediamine compound is 1,4-phenylenediamine.

A further aspect of the present invention provides a method of reducing or inhibiting fouling and deposit formation during hydrocarbon processing including the step of administering an effective amount of one or more water-soluble compounds of the following formula to a hydrocarbon stream at or upstream of a location where said fouling and/or said deposit formation may occur:

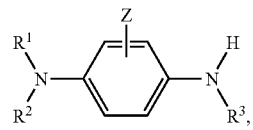

wherein at least one of $R^1$, $R^2$, and $R^3$ is

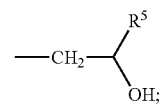

$R^1$, $R^2$ and $R^3$ are independently selected from H, $C_1$-$C_{18}$ alkyl, hydroxyalkyl, —O—$R^6$, —S—$R^6$, —N—($R^7$) ($R^8$), aryl, and

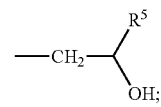

$R^5$ is selected from the group consisting of H, alkyl, hydroxyalkyl, —O—$R^6$, —S—$R^6$, —N—($R^7$)($R^8$), and aryl;

Z comprises one or more substituents selected from the group consisting of hydrogen, alkyl, alkenyl, alkynyl, cycloalkyl, cycloalkenyl, aryl, heterocyclo, —CN, —NO$_2$, —O—$R^6$, —S—$R^6$, and —N($R^7$)($R^8$);

$R^6$, $R^7$ and $R^8$ are independently selected form the group consisting of hydrogen, alkyl, alkenyl, alkynyl, cycloalkyl, cycloalkenyl, aryl and heterocyclo; and wherein said composition is water-soluble.

DETAILED DESCRIPTION OF THE INVENTION

The present invention includes compounds of the formula:

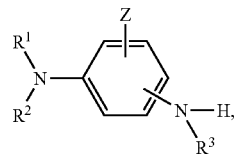

wherein the NHR$^3$ group may be present in any of the ortho, para, and meta positions, at least one of $R^1$, $R^2$, and $R^3$ is

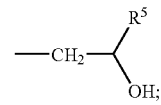

$R^1$, $R^2$ and $R^3$ are independently selected from H, alkyl, hydroxyalkyl, —O—$R^6$, —S—$R^6$, —C(O)$R^6$, —C(S)$R^6$, —N—$(R^7)(R^8)$, aryl, and

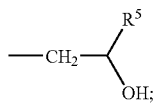

$R^5$ is selected from the group consisting of H, alkyl, hydroxyalkyl, O, S, —O—$R^6$, —S—$R^6$, —N—$(R^7)(R^8)$, and aryl;

Z comprises one or more substituents selected from the group consisting of hydrogen, alkyl, alkenyl, alkynyl, cycloalkyl, cycloalkenyl, aryl, heterocyclo, —CN, —$NO_2$, —O—$R^6$, —S—$R^6$, and —N$(R^7)(R^8)$; and $R^6$, $R^7$ and $R^8$ are independently selected from the group consisting of hydrogen, alkyl, alkenyl, alkynyl, cycloalkyl, cycloalkenyl, aryl and heterocyclo. Desirably, the second amine group is in the para position, corresponding to the following formula:

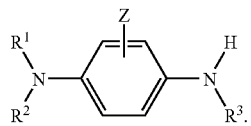

The term "alkyl" is meant to include substituted or unsubstituted, straight or branched chain saturated hydrocarbon groups, desirably having 1 to 20 carbons in the main chain. Examples of unsubstituted groups include methyl, ethyl, propyl, isopropyl, n-butyl, t-butyl, isobutyl, pentyl, hexyl, isohexyl, heptyl, 4,4-dimethyl pentyl, octyl, 2,2,4-trimethylpentyl, nonyl, decyl, undecyl, dodecyl, and the like. Substituents may include halogen, hydroxy, or aryl groups.

The term "hydroxyalkyl" is meant to include an alkyl group as described above with at least one hydroxy group substituent.

The term "alkenyl" is meant to include substituted or unsubstituted, straight or branched chain hydrocarbon groups including at least one carbon to carbon double bond in the chain, and desirably including 2 to 10 carbons in the normal chain. Examples of such unsubstituted alkenyl groups include ethenyl, propenyl, isobutenyl, butenyl, pentenyl, hexenyl, heptenyl, octenyl, nonenyl, decenyl, and the like. Substituents may include those as described above.

The term "alkynyl", is meant to include substituted or unsubstituted, straight and branched chain hydrocarbon groups including at least one carbon to carbon triple bond in the chain, and preferably having 2 to 10 carbons in the normal chain. Examples of such unsubstituted groups include ethynyl, propynyl, butynyl, pentynyl, hexynyl, heptynyl, octynyl, nonynyl, decynyl, and the like. Substituents may include those as described above.

The term "cycloalkyl" is meant to include substituted or unsubstituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "cycloalkenyl" is meant to include hydrocarbon ring systems which may be substituted or unsubstituted as described above for cycloalkyl, further containing at least one carbon to carbon double bond forming a partially unsaturated ring. These may also include substituents as described above.

The terms "heterocyclo" or "heterocyclic" are meant to include substituted or unsubstituted, fully saturated or unsaturated, aromatic or non-aromatic cyclic groups having at least one heteroatom (such as N, O, and S) in at least one ring, desirably monocyclic or bicyclic groups having 3-6 atoms in each ring. The heterocyclo group may be bonded through any carbon or heteroatom of the ring system. Examples of heterocyclic groups include, without limitation, thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. These may also include substituents as described above.

The term "aryl" is meant to include substituted or unsubstituted monocyclic, bicyclic or tricyclic aromatic groups, desirably including one or two rings which contain only carbon ring atoms and 6 to 12 ring carbons. The term "aryl" can also refer to an aryl group fused to a monocyclic cycloalkyl or monocyclic heterocycle in which the point(s) of attachment is/are on the aromatic portion. Examples of aryl groups include phenyl, biphenyl, and naphthyl. Aryl rings fused to cycloalkyls are include indanyl, indenyl, and tetrahydronaphthyl. Examples of aryl groups fused to heterocyclic groups include 2,3-dihydrobenzofuranyl, benzopyranyl, 1,4-benzodioxanyl, and the like. Substituents may include those as described above as well as nitro groups.

The water-soluble phenylenediamine compounds of the present invention may be formed by the reaction of a phenylenediamine compound of the following formula:

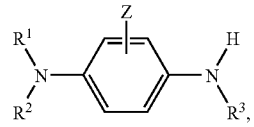

wherein at least one of $R^1$, $R^2$ and $R^3$ is H;

$R^1$, $R^2$ and $R^3$ are independently selected from the group consisting of, alkyl, hydroxyalkyl, —O—$R^6$, —S—$R^6$, —C(O)$R^6$, —C(S)$R^6$, —N—$(R^7)(R^8)$, and aryl;

Z comprises one or more substituents selected from the group consisting of hydrogen, alkyl, alkenyl, alkynyl, cycloalkyl, cycloalkenyl, aryl, heterocyclo, —CN, —$NO_2$, —O—$R^6$, —S—$R^6$, and —N$(R^7)(R^8)$; and $R^6$, $R^7$ and $R^8$ are independently selected from the group consisting of hydrogen, alkyl, alkenyl, alkynyl, cycloalkyl, cycloalkenyl, aryl and heterocyclo, with a heterocylic compound of the following formula:

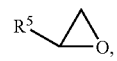

wherein $R^5$ is selected from the group consisting of H, alkyl, hydroxyalkyl, —O—$R^6$, —S—$R^6$, —N—$(R^7)(R^8)$, and aryl. Desirably, the heterocyclic compound is propylene oxide or butylene oxide.

This reaction produces a mixture of reaction products that may be separated by any of a variety of means known in the art, including chromatography. For example, the reaction of 1,4-phenylenediamine with the substituted heterocyclic compound may produce a mixture of five different products as shown in the following reaction scheme:

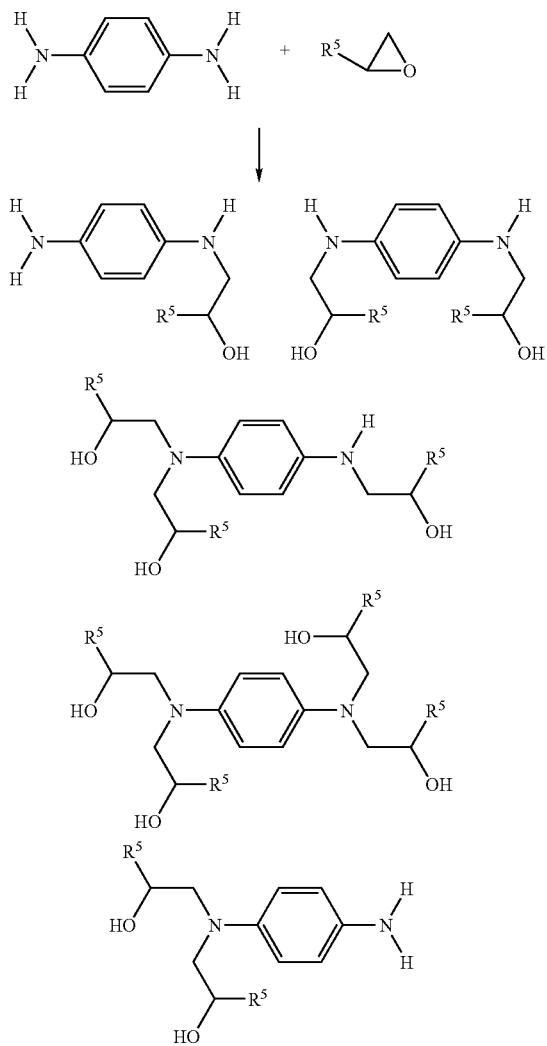

Similarly, where the phenylenediamine starting material includes a non-hydrogen substitution, the products of the reaction with the substituted heterocyclic compound are shown by the reaction scheme as shown below.

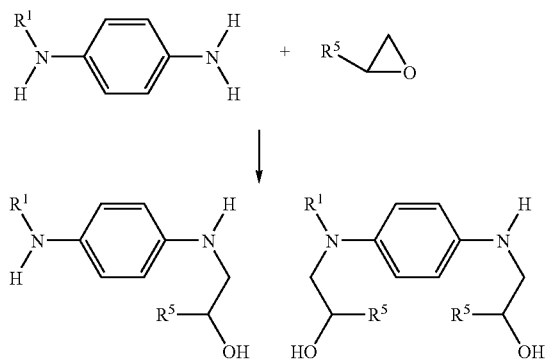

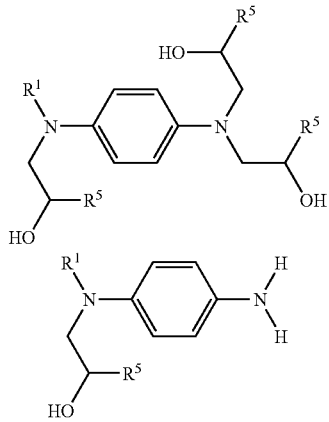

The reaction of 1,4-phenylenediamine with propylene oxide will also produce a mixture of products which include N,N'-dihydroxypropylphenylenediamine, N,N-dihydroxypropylphenylenediamine, N-hydroxypropylphenylenediamine, N,N,N'-trihydroxypropylphenylenediamine, and N,N,N',N'-tetrahydryoxypropylphenylenediamine.

The phenylenediamine compounds of the present invention are useful as antioxidant/free-radical polymerization inhibitors. In other words, they are useful to stabilize hydrocarbon compositions including ethylenically unsaturated monomers by inhibiting polymerization. They are useful as inhibitors under both process and storage conditions including where the monomers are subjected to elevated temperatures, for example up to about 125° C.

The water-soluble phenylenediamine compositions are useful with a variety of ethylenically unsaturated monomers. These include, but are not limited to vinyl aromatic compounds such as styrene, substituted styrene, divinylbenzene, vinyl toluene, and vinyl naphthalene, and other ethylenically unsaturated monomers such as acrylic acid, alkyl acrylates, acrylonitrile, butadiene, dicyclopentadiene, cyanoacrylates, isoprene, and propylene.

For the methods of the present invention, the useful water-soluble phenylenediamine compositions will retain at least one "—NH" group for effective polymerization inhibition. The effective amount of the water-soluble phenylenediamine composition having at least one "—NH" group used in the methods of the present invention as a polymerization inhibitor is that amount which is sufficient to affect inhibition of polymerization and will vary according to the conditions under which the monomer is synthesized, processed, and/or stored. There are several factors that will affect the amount of inhibitor that is required. Factors that will require an increase in the amount of inhibitor are increased monomer concentration and increased temperature.

Generally, an effective concentration of the water-soluble phenylenediamine compositions of the present invention will range from about 0.5 ppm to about 2000 ppm, more desirably from about 1 ppm to about 50 ppm. The compositions may be used in many hydrocarbon processing steps where premature polymerization is likely to occur including hydrocarbon cracking processes, preheating, distillation, hydrogenation, extraction, etc. The water-soluble phenylenediamine composition may be added at a location upstream of these process locations.

The water-soluble phenylenediamine compositions may be added to a water stream, hydrocarbon stream or to a monomer composition alone, or after first being premixed with a solvent. Where a premix of the water-soluble phenylenediamine composition is desired, it may be first combined with a solvent such as water or an organic solvent including, but not limited to methanol, ethanol, acetone, pyridine, nitrobenzene, n-hexadecane, n-hexane, methylene chloride, dimethyl sulphoxide, chloroform, carbon tetrachloride, benzene, glycols, esters and ethers.

Other inhibitors or antifoulants known in the art may be combined with the water-soluble phenylenediamine compounds of the present invention. These may include other phenylenediamines, hydroxylamines, nitroxides, and hindered phenols. When a compositions containing an additional phenylenediamine composition is desired, the additional phenylenediamine may correspond to the following formula:

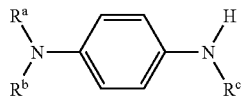

wherein $R^a$, $R^b$ and $R^c$ are independently selected from the group consisting of H, $C_1$-$C_{18}$ alkyl, hydroxyalkyl, —O—$R^6$, —S—$R^6$, —N—($R^7$)($R^8$), and aryl.

The water-soluble phenylenediamine compositions of the present invention have a wider variety of uses as compared to conventional phenylenediamine inhibitors. For example, during processing of acrylonitrile, there is contact with water and consequent fouling and deposit formation in the water sections. A phenylenediamine composition that is not water-soluble will not be effective as an inhibitor in this situation.

PDA's such as N-(1,4-dimethylpentyl)-N'-phenyl-p-phenylenediamine and N-(1,3-dimethylbutyl)-N-phenyl-p-phenylenediamine are not miscible with water. Instead, when they are added to water, they separate, forming two distinct layers, a PDA layer and a water layer. However, the PDA's of the present invention are completely miscible with water. When they are added to water, the PDA's of the present invention do not form a separate layer, i.e., a partition between the aqueous and hydrocarbon phases where it provides vinyl monomer free radical polymerization inhibition.

The features and advantages of the present invention are more fully shown by the following examples which are provided for purposes of illustration, and are not to be construed as limiting the invention in any way.

EXAMPLES

Acrylonitrile was chosen to represent reactive vinyl monomers. The water-soluble phenylenediamines (PDA's) of the present invention were tested in acrylonitrile. Comparative testing was also performed using conventional polymerization inhibitors. The comparative inhibitor compositions are shown in TABLE 1, while the inventive inhibitor compositions which were tested are shown in TABLE 2. The parenthesis after the inhibitor names indicates the weight ratio of two or more inhibitors in the composition.

TABLE 1

Comparative Inhibitor Compositions

| Composition | Inhibitor(s) |
|---|---|
| A | Blank |
| B | Hydroquinone |
| C | N-(1,3-dimethylbutyl)-N-phenyl-p-phenylenediamine |
| D | Benzoquinonediimide |
| E | Benzoquinonediimide/Hydroquinone (1:1) |
| F | Hydroquinone/N-(1,3-dimethylbutyl)-N-phenyl-p-phenylenediamine (1:1) |
| G | Hydroquinone/N-(1,4-dimethylpentyl)-N'-phenyl-p-phenylenediamine (1:1) |
| H | N-(1,4-dimethylpentyl)-N'-phenyl-p-phenylenediamine |

TABLE 2

Inventive Inhibitor Compositions

| Composition | Inhibitor(s) |
|---|---|
| I | N,N,N',N'-Tetrahydroxypropylphenylenediamine |
| J | N-hydroxypropylphenylenediamine and N,N'-dihydroxypropylphenylenediamine (reaction mixture) |
| K | N-hydroxypropylphenylenediamine and N,N'-dihydroxypropylphenylenediamine (reaction mixture)/Hydroquinone (1:1) |
| L | N-hydroxypropylphenylenediamine and N,N'-dihydroxypropylphenylenediamine (reaction mixture)/Benzoquinonediimide (1:1) |

For each of the experiments, acrylonitrile was heated under an inert atmosphere in glass tubes. A single inhibitor composition (A-L) was added to each tube. In the first experiment, tubes containing acrylonitrile were dosed with 2 ppm of various inhibitors and were heated at 110° C.

For the second experiment, 35 ppm azobisobutyronitrile (AIBN), a free radical polymerization initiator, was also added to each tube to simulate conditions where free radical concentrations are relatively high. The second experiment was conducted at 66° C.

For each experiment, the performance of the inhibitor performance was judged by the length of the induction time for polymerization, i.e., the formation of visible polymer, as the reaction mixture turned turbid and white polyacrylonitrile started to deposit. The results of both experiments are shown in TABLE 3, below.

TABLE 3

Results of Acrylonitrile Study

| | Induction Time to Polymerization | |
|---|---|---|
| Composition | Experiment 1 (hours) | Experiment 2 (with polymerization initiator) (minutes) |
| A | 1 | 15 |
| B | 2.2 | 132 |
| C | 106 | n/a |
| D | 508 | n/a |
| E | 528 | 160 |
| F | n/a | 183 |
| G | n/a | 195 |
| H | n/a | 230 |
| I | 4 | 49 |
| J | 106 | 290 |
| K | 168 | n/a |
| L | 278 | n/a |

As can be seen from TABLE 3, the inventive compositions J, K and L performed better than the comparative compositions that included the known polymerization inhibitors hydroquinone, N-(1,4-dimethylpentyl)-N'-phenyl-p-phenylenediamine, and N-(1,3-dimethylbutyl)-N-phenyl-p-phenylenediamine. In addition, inventive composition J has the advantage of being water-soluble which increases the variety of potential uses.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A method of reducing or inhibiting fouling and deposit formation during hydrocarbon processing comprising the step of administering to a hydrocarbon stream at or upstream of a location where said fouling and/or said deposit formation may occur an effective amount of a first polymerization inhibitor composition comprising one or more water-soluble compounds of the following formula:

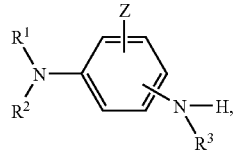

wherein at least one of $R^1$, $R^2$, and $R^3$ is

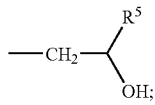

$R^1$, $R^2$ and $R^3$ are independently selected from H, $C_1$-$C_{18}$ alkyl, hydroxyalkyl, —O—$R^6$, —S—$R^6$, —N—($R^7$)($R^8$), aryl, and

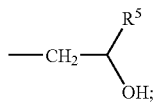

$R^5$ is selected from the group consisting of H, alkyl, hydroxyalkyl, —O—$R^6$, —S—$R^6$, —N—($R^7$)($R^8$), and aryl;

Z comprises one or more substituents selected from the group consisting of hydrogen, alkyl, alkenyl, alkynyl, cycloalkyl, cycloalkenyl, aryl, heterocyclo, —CN, —$NO_2$, —O—$R^6$, —S—$R^6$, and —N($R^7$)($R^8$);

$R^6$, $R^7$ and $R^8$ are independently selected from the group consisting of hydrogen, alkyl, alkenyl, alkynyl, cycloalkyl, cycloalkenyl, aryl and heterocyclo; and wherein said composition is water-soluble.

2. The method of claim 1, further comprising the step of mixing said water-soluble compounds with a solvent prior to said administering.

3. The method of claim 1, wherein at least one of said compounds in said first polymerization inhibitor composition corresponds to the following formula:

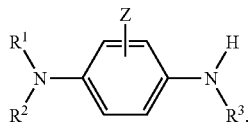

4. The method of claim 2, wherein the solvent is selected from the group consisting of water and an organic solvent.

5. The method of claim 1, further comprising administering to the hydrocarbon stream a second polymerization inhibitor composition.

6. The method of claim 5, wherein said second polymerization inhibitor composition is a phenylenediamine of the following formula:

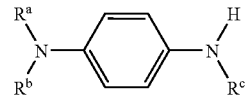

wherein $R^a$, $R^b$ and $R^c$ are independently selected from the group consisting of H, $C_1$-$C_{18}$ alkyl, hydroxyalkyl, —O—$R^6$, —S—$R^6$, —N—($R^7$)($R^8$), and aryl.

7. The method of claim 1, wherein said first polymerization inhibitor composition comprises a compound of the following formula:

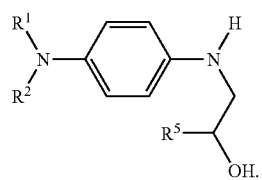

8. The method of claim 1, wherein said first polymerization inhibitor composition comprises at least one of the following compounds:

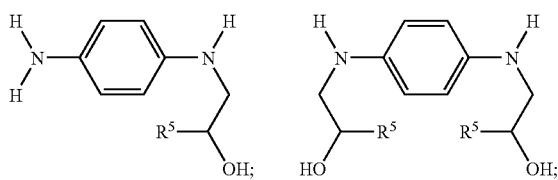

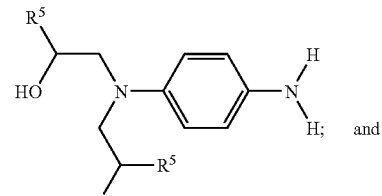

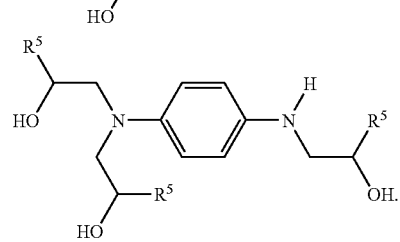

9. The method of claim 1, wherein said first polymerization inhibitor composition comprises at least one of the following compounds:

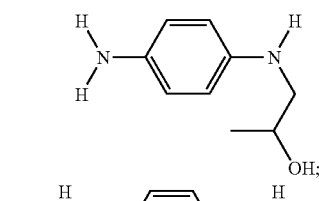

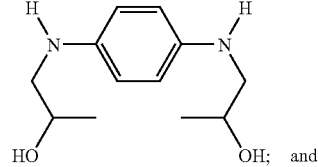

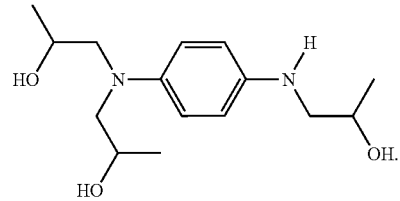

* * * * *